United States Patent
Boden, Jr. et al.

(10) Patent No.: US 10,518,069 B2
(45) Date of Patent: Dec. 31, 2019

(54) IMPLANTABLE VALVE ASSEMBLY WITH EXTENDED LIFESPAN

(71) Applicant: Integra LifeSciences Switzerland Sarl, Le Locle (CH)

(72) Inventors: Thomas Boden, Jr., Middleboro, MA (US); Alan J. Dextradeur, Franklin, MA (US)

(73) Assignee: Integra LifeSciences Switzerland Sarl, Le Locle (CH)

( * ) Notice: Subject to any disclaimer, the term of this patent is extended or adjusted under 35 U.S.C. 154(b) by 273 days.

(21) Appl. No.: 15/337,827

(22) Filed: Oct. 28, 2016

(65) Prior Publication Data

US 2018/0117289 A1    May 3, 2018

(51) Int. Cl.
*A61M 27/00* (2006.01)
*A61M 25/00* (2006.01)

(52) U.S. Cl.
CPC ...... *A61M 27/006* (2013.01); *A61M 25/0071* (2013.01); *A61M 25/007* (2013.01)

(58) Field of Classification Search
CPC .................. A61M 27/006; A61M 25/0071
See application file for complete search history.

(56) References Cited

U.S. PATENT DOCUMENTS

| 3,583,404 | A | | 6/1971 | McWhorter |
| 3,626,950 | A | | 12/1971 | Schulte |
| 3,669,116 | A | | 6/1972 | Heyer |
| 4,382,445 | A | | 5/1983 | Sommers |
| 4,583,967 | A | | 4/1986 | Harris |
| 4,595,390 | A | | 6/1986 | Hakim et al. |
| 4,767,400 | A | | 8/1988 | Miller et al. |
| 4,950,232 | A | | 8/1990 | Ruzicka et al. |
| 5,002,528 | A | | 3/1991 | Palestrant |
| 5,052,998 | A | | 10/1991 | Zimmon |
| 5,066,278 | A | * | 11/1991 | Hirschberg ....... A61M 5/14276 604/246 |

(Continued)

OTHER PUBLICATIONS

Lin et al., "Computational and Experimental Study of Proximal Flow in Ventricular Catheters," J. Neurosurg 99:426-431 (2003).

(Continued)

*Primary Examiner* — Ariana Zimbouski
(74) *Attorney, Agent, or Firm* — Cohen & Hildebrand, PLLC (57) ABSTRACT

An implantable valve assembly including a drainage catheter having a central lumen transitioning into a plurality of distinct branch lumen made of a shape memory material. A bioabsorbable dip coating secures the distal end of the plural distinct branch lumen together in physical contact with one another. Each branch lumen has an outer perimeter comprising at least one of a first outer surface section and a second outer surface section. In a secured state with the plural distinct branch lumen held together by the dip coating fluid is prohibited from passing through the holes defined in the first outer surface section. Bioabsorbable blocking members disposed about the outer perimeter of the assembled branch lumen mask holes defined in the second outer surface section prohibiting fluid from entering therein. In a time staggered fashion, the bioabsorbable elements absorb exposing new holes through which the fluid drains.

29 Claims, 7 Drawing Sheets

(56) References Cited

U.S. PATENT DOCUMENTS

| | | | |
|---|---|---|---|
| 5,201,724 | A | 4/1993 | Hukins et al. |
| 5,514,112 | A | 5/1996 | Chu et al. |
| 6,913,589 | B2 | 7/2005 | Dextradeur et al. |
| 7,037,288 | B2 | 5/2006 | Rosenberg et al. |
| 7,226,441 | B2 | 6/2007 | Kulessa |
| 7,582,068 | B2 | 9/2009 | Koullick et al. |
| 7,763,142 | B2 | 7/2010 | Watson |
| 7,850,706 | B2 | 12/2010 | Regner et al. |
| 7,976,517 | B2 | 7/2011 | Dextradeur et al. |
| 8,088,091 | B2 | 1/2012 | Thomas et al. |
| 8,221,392 | B2 | 7/2012 | Dextradeur et al. |
| 8,376,980 | B2 | 2/2013 | Watson |
| 8,827,944 | B2 | 9/2014 | Sevrain |
| 8,852,156 | B2 | 10/2014 | Olson et al. |
| 2002/0123713 | A1 | 9/2002 | Watson |
| 2003/0135148 | A1* | 7/2003 | Dextradeur ....... A61M 25/0662 604/8 |
| 2003/0216710 | A1 | 11/2003 | Hurt |
| 2005/0080399 | A1 | 4/2005 | Bolmsjo et al. |
| 2005/0277862 | A1* | 12/2005 | Anand ............... A61M 25/0068 604/4.01 |
| 2007/0142817 | A1 | 6/2007 | Hurt |
| 2007/0179426 | A1 | 8/2007 | Belden |
| 2008/0082036 | A1 | 4/2008 | Trescony et al. |
| 2008/0183128 | A1* | 7/2008 | Morriss ............... A61M 3/0283 604/35 |
| 2008/0281250 | A1 | 11/2008 | Bergsneider et al. |
| 2009/0156999 | A1* | 6/2009 | Adams ................ A61M 25/005 604/103.09 |
| 2010/0042039 | A1 | 2/2010 | Trescony et al. |
| 2011/0282264 | A1 | 11/2011 | Hurt |
| 2012/0078159 | A1 | 3/2012 | Wilson et al. |
| 2012/0078220 | A1 | 3/2012 | Fallin et al. |
| 2013/0253445 | A1* | 9/2013 | Nimkar ............... A61M 25/001 604/264 |
| 2014/0207043 | A1 | 7/2014 | Anand et al. |
| 2014/0207045 | A1 | 7/2014 | Anand et al. |
| 2014/0228734 | A1 | 8/2014 | Wilson et al. |
| 2014/0288479 | A1 | 9/2014 | Mohan et al. |
| 2015/0196497 | A1* | 7/2015 | McGonigle .......... A61K 9/7007 424/425 |
| 2015/0202406 | A1* | 7/2015 | Lim .................... A61M 25/007 604/528 |
| 2015/0297874 | A1* | 10/2015 | East .................... A61M 27/006 604/9 |
| 2017/0049554 | A1* | 2/2017 | Li ...................... A61M 39/0247 |
| 2017/0127929 | A1* | 5/2017 | Schutt .................. A61B 1/307 |

OTHER PUBLICATIONS www.alcyonels.com/hydrocephalus, Alcyone Lifesciences Inc. website; publication date indicated at bottom of website (2016), printed on Oct. 25, 2016 (p. 3).

\* cited by examiner

IMPLANTABLE VALVE ASSEMBLY WITH EXTENDED LIFESPAN

BACKGROUND OF THE INVENTION

Field of the Invention

The present invention relates to a valve for implantation in the body. More particularly, the invention relates to an improved valve assembly for implantation in the body to drain a bodily fluid, in particular, cerebral spinal fluid (CSF), wherein the catheter is specifically designed to extend its operational lifespan in the presence of undesirable obstruction or clogging that restricts the flow of bodily fluid therethrough.

Description of Related Art

Catheters are used to perform various diagnostic and therapeutic procedures at target sites within the body. One such use for catheters is in treating the condition of hydrocephalus. Hydrocephalus is the accumulation of cerebrospinal fluid (CSF) in the brain, resulting from increased production, or more commonly, pathway obstruction or decreased absorption of the fluid. Cerebrospinal fluid is a clear, colorless fluid that is primarily produced by the choroid plexus and surrounds the brain and spinal cord. Shunts have been used for decades for the treatment of hydrocephalus. CSF shunts establish an accessory pathway for the movement of CSF to bypass an obstruction of the natural pathways.

Figure 1:
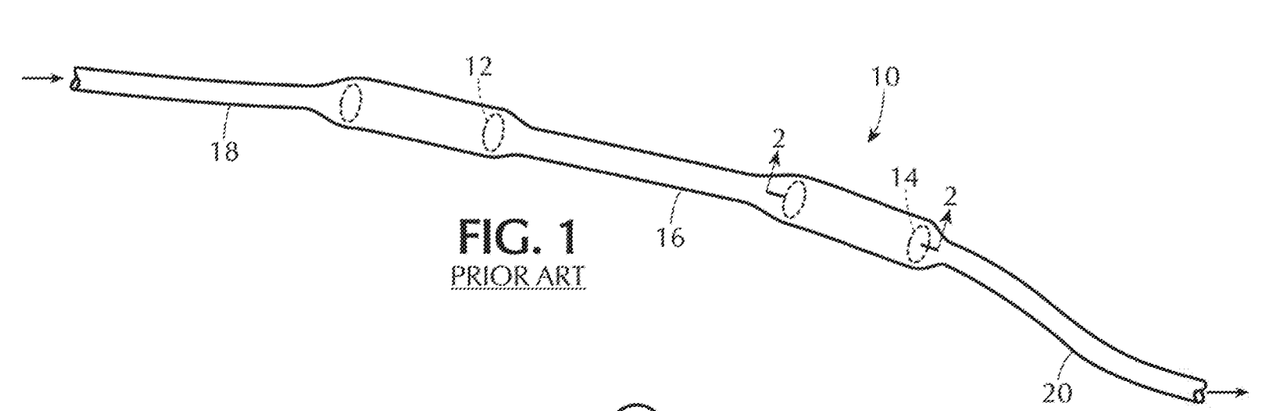
FIG. 1 is a perspective view of a prior art shunt valve assembly including two shunt valves.

The shunt is positioned to enable the CSF to be drained from the cerebral ventricles or sub-arachnoid spaces into another absorption site (e.g., the right atrium of the heart or the peritoneal cavity) through a system of relatively small catheters. FIG. 1 is an exemplary illustration of a conventional shunt valve assembly 10 disclosed in U.S. Pat. No. 4,595,390, which is herein incorporated by reference in its entirety. The shunt valve assembly 10 includes one or more one-way shunt valves 12, 14 separated by a pumping chamber 16 that maintain the CSF flowing away from the brain and moderate the pressure or flow rate. Ventricular catheter 18 is connected to the inlet of the valve assembly while a drainage catheter 20 is connected to the outlet of the valve assembly. Ventricular catheter 18 has a plurality of pores, holes or openings defined in its walls proximate its distal end for receiving therethrough the CSF from the ventricle. The diameter of such pores is relatively small (generally, approximately 0.25 mm-approximately 0.50 mm; or approximately 250 micrometers-approximately 500 micrometers). The drainage system using catheters and valves enables the excess CSF within the brain to be evacuated and, thereby, the pressure within the cranium to be maintained within an appropriate range. This valve assembly may be surgically implanted using well known procedures. During implantation a burr hole is bored through the skull. A stylet is typically utilized as an introducer to properly position the ventricular catheter made of a flexible material (e.g., soft plastic tube) at the desired target site within the brain ventricle. The valve and drainage catheters are fluidly connected to a reservoir disposed proximate the burr hole under the skin. The CSF enters the distal holes of the ventricular catheter and is transported to the abdomen by the drainage catheter. Flow of CSF fluid away from the brain is insured by the one way shunt valve.

At tremendous cost to the health care system ranging in billions of dollars, each year tens of thousands of invasive brain surgeries are required to replace or revise hydrocephalus shunts that have malfunctioned due to mechanical failure. Blockage, occlusion or clogging of the relatively small diameter pores defined in the wall of the catheter, primarily in the ventricular catheter, is the leading cause of mechanical shunt failure and malfunction in hydrocephalus treatment. Specifically, the distal holes defined in the ventricular catheter become occluded and blocked when choroid plexus (a fibrous tissue in the ventricles that produces CSF), blood and other debris enters the openings due to the pulsatile nature of CSF circulation. Those pores defined in the wall of the catheter that are closest to its proximal end are particularly susceptible to undesirable blockage due to its close physical proximity to the choroid plexus. To reduce the occurrence of such growth, the catheter is ideally positioned in an area away from the choroid plexus and not in close proximity to the ventricular wall. Despite such efforts, entry of the choroid plexus and other debris into the pores of the catheter may still occur partially or completely obstructing the openings and, in turn, hampering or even prohibiting removal of the catheter if blockage becomes to significant.

It is therefore desirable to develop an improved implantable drainage catheter for the drainage of CSF or other bodily fluid having an extended operational lifespan despite obstruction and clogging of the pores defined in its wall.

SUMMARY OF THE INVENTION

An aspect of the present invention is an improved implantable drainage catheter for the drainage of CSF or other bodily fluid having an extended operational lifespan despite obstruction and clogging of the pores defined in its wall.

The present invention is directed to an implantable valve assembly including a drainage catheter having a central lumen transitioning into a plurality of distinct branch lumen made of a shape memory material. A bioabsorbable dip coating secures the distal end of the plural distinct branch lumen together in physical contact with one another. Each branch lumen has an outer perimeter comprising at least one of a first outer surface section and a second outer surface section. In a secured state with the plural distinct branch lumen held together by the dip coating fluid is prohibited from passing through the holes defined in the first outer surface section. Bioabsorbable blocking members disposed about the outer perimeter of the assembled branch lumen mask holes defined in the second outer surface section prohibiting fluid from entering therein. In a time staggered fashion, the bioabsorbable elements absorb exposing new holes through which the fluid drains.

The invention is further directed to a method for using the implantable valve assembly as described in the preceding paragraph. The method comprising the steps of during implantation, advancing the drainage catheter to a target site while the plural distinct branch lumen are secured in direct physical contact with one another from the distal end of the drainage catheter to the interface of the central lumen via the dip coating. While in a secured state with the plural distinct branch lumen held together by the dip coating: (i) the first outer surface section of each of the plural distinct branch lumen is in direct physical contact with the first outer surface section of at least one other branch lumen in a longitudinal direction from the interface with the central lumen to the distal end of the catheter prohibiting fluid from entering holes defined in the first outer surface sections of any of the plural distinct branch lumen; and (ii) the second outer surface section of each of the plural distinct branch lumen is not in physical contact with either the first or second outer surface sections of any other branch lumen.

BRIEF DESCRIPTION OF THE DRAWING

The foregoing and other features of the present invention will be more readily apparent from the following detailed description and drawings of illustrative embodiments of the invention wherein like reference numbers refer to similar elements throughout the several views and in which.

DETAILED DESCRIPTION OF THE INVENTION

By way of illustrative example only, the present invention is shown and described as an implantable catheter for the drainage of a bodily fluid, for example, CSF. It is contemplated and within the intended scope of the present invention for the implantable catheter to be employed for the drainage of other types of bodily fluid.

The terms "proximal"/"proximally" and "distal"/"distally" refer to a direction closer to or away from, respectively, an operator (e.g., surgeon, physician, nurse, technician, user, etc.) who would insert the medical device into the patient, with the opposite tip-end (i.e., distal end or leading end) of the device inserted inside a patient's body. Thus, for example, a "proximal direction" would refer to the direction towards the operator, whereas "distal direction" would refer to the direction away from the operator towards the leading or tip-end of the medical device.

Figure 2A:
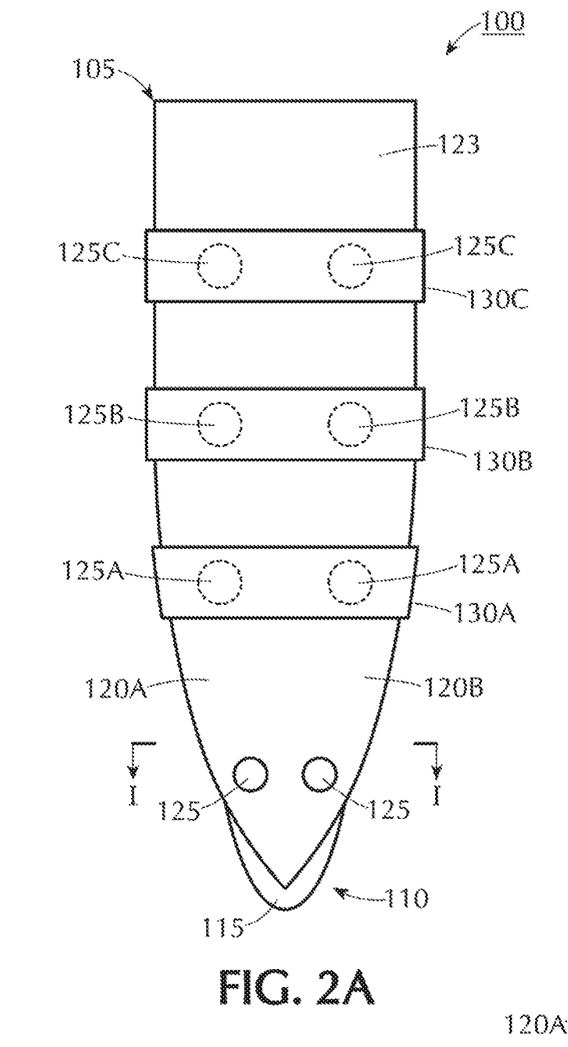
FIG. 2A is a partial side view of a distal end of an exemplary drainage catheter in accordance with the present invention, prior to implantation in the human body, having two branch lumen.

FIG. 2A is a partial side view of a distal end of an exemplary drainage catheter 100 in accordance with the present invention, prior to implantation into the human body or body of an animal. Catheter 100 has a proximal end 105 and an opposite distal end 110. The distal end 110 of the catheter 100 is split or separable into a plurality of two or more distinct branch lumen 120 each having its own passageway defined therethrough. In the exemplary embodiment illustrated in FIG. 2A, the catheter 100 has two distinct branch lumen 120a, 120b. Any number of two or more separable distinct branch lumen 120 are possible and within the intended scope of the present invention. Regardless of the number, the plural distinct branch lumen at the distal end of the catheter all feed into a single common or shared central lumen 123 at the opposite proximal end 105 of the catheter. Each distinct branch lumen is preferably approximately 2 cm in length as measured from its most distal tip of the catheter to an interface with the single central lumen.

The present invention will hereinafter be described with respect to the illustrative embodiment in FIG. 2A in which the catheter 100 has two distinct branch lumen 120a, 120b. However, similar principles and description apply regardless of the number of two or more branch lumen. Branch lumen 120a, 120b are made of a shape memory material, that is deformable upon the application of an external force, but automatically returns to its original (non-deformed) shape when the applied external force is withdrawn or removed. By way of non-limiting examples, the shape memory material may be a shape memory metal (e.g., Nitinol (NiTi) alloys) and/or a shape memory polymer (e.g., Poly(methyl methacrylate) (PMMA), polyurethanes (PU), poly(ethylene terephthalate) (PET), or polystyrenes (PS)). In its non-deformed shape (i.e., in the absence of the applied external force) the plural branch lumen 120a, 120b extend radially outward from the common central lumen 123 like petals of a flower. Upon the application of an external force, the distinct branch lumen 120a, 120b are deformable radially inward so as to physically contact one another in a longitudinal direction from its distal end to the interface with the common central lumen. The assembled distinct branch lumen together form a tube-like structure having the same diameter and coaxial with that of the central lumen 123.

Prior to implantation, a dip coating or covering 115 is disposed at the distal end 110 of the catheter 100. On the one hand, the dip coating or covering 115 is made of a material sufficient to secure the separable plural distinct branch lumen 120a, 120b together and prevent separation from one another during insertion of the drainage catheter 100 via a ventricle or other body passageway to a target site in the body. On the other hand, the dip coating or covering 115 is made of a bioabsorbable, biodegradable or bioresorbable material, i.e., a material that dissolves in the body once its intended purpose has been served (i.e., upon expiration of time $t_1$, preferably with the range of approximately 72 hrs. to 168 hrs. (one week)). For instance, the bioabsorbable, biodegradable or bioresorbable material may be a polymer or copolymers made from lactic acid or glycolic acid.

The outer perimeter of each of the plural distinct branch lumen 120a, 120b includes a first outer surface section 135 and a second outer surface section 140. Together the first and second outer surface sections 135, 140 of a particular branch lumen comprise its entire outer radial perimeter. Prior to implantation, while in a secured or assembled state with the plural distinct branch lumen 120a, 120b held together by the dip coating 115: (i) the first outer surface section 135 of each of the plural distinct branch lumen is in direct physical contact with the first outer surface section 135 of at least one other branch lumen; (ii) while the second outer surface section 140 of each of the plural distinct branch lumen is not in physical contact with the first or second outer surface sections of any other distinct branch lumen. As clearly illustrated in FIG. 2B depicting a cross-sectional view of the catheter of FIG. 2A along line I-I, prior to implantation, when the plural distinct branch lumen 120a, 120b are assembled or secured together by the dip coating or covering 115 the first outer surface section 135 of each of the two branch lumen 120a, 120b are in physical contact with one another in a longitudinal direction from the interface with the central lumen 123 to the distal end 110 of the catheter.

Figure 3A:
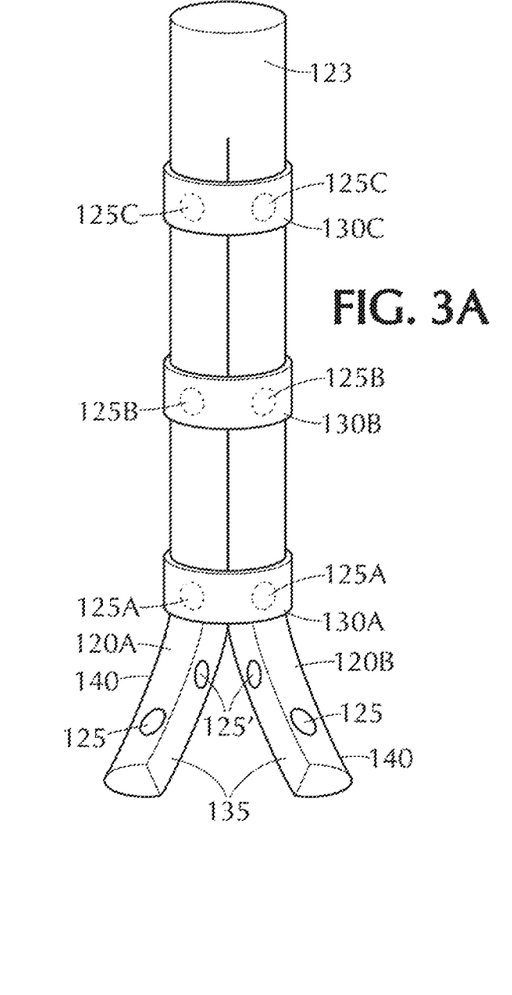
FIGS. 3A-3D are partial side views of the drainage catheter of FIG. 2A at four different stages in time.
Figure 3B:
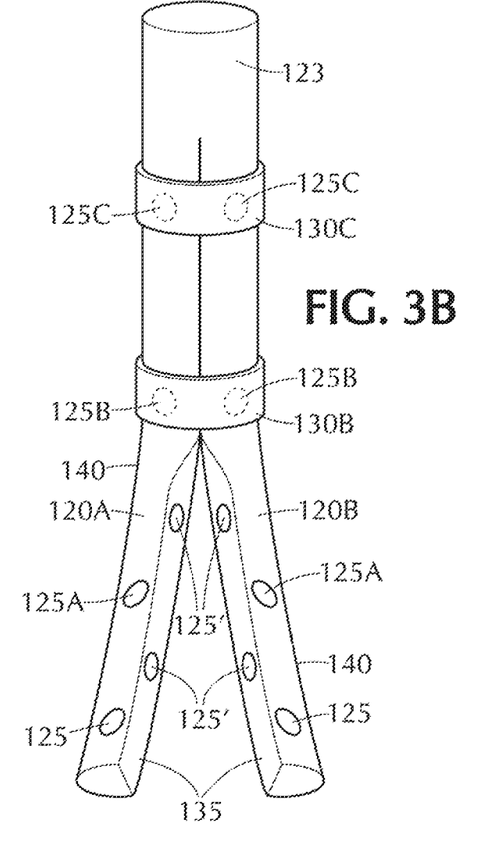
Figure 3C:
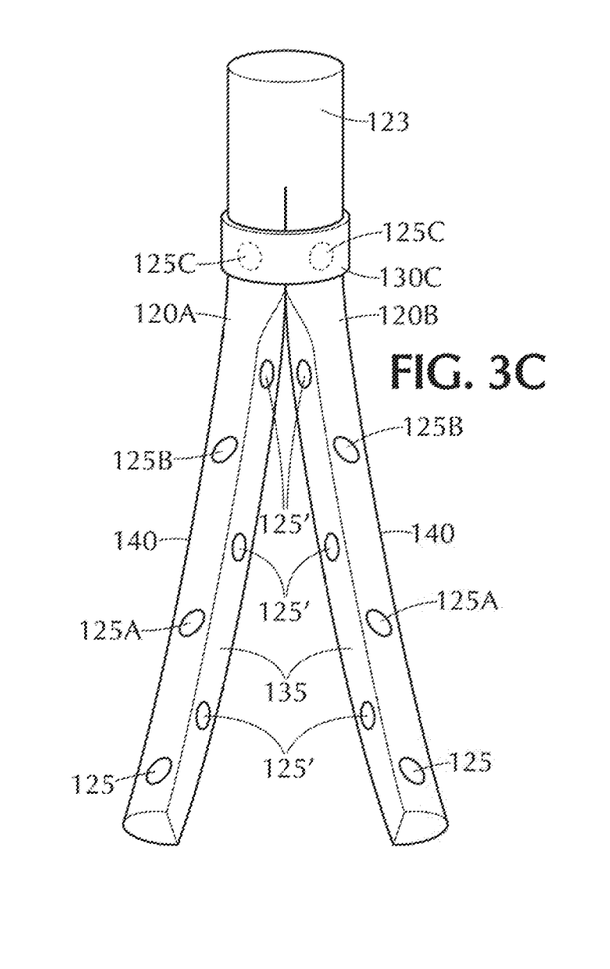
Figure 3D:
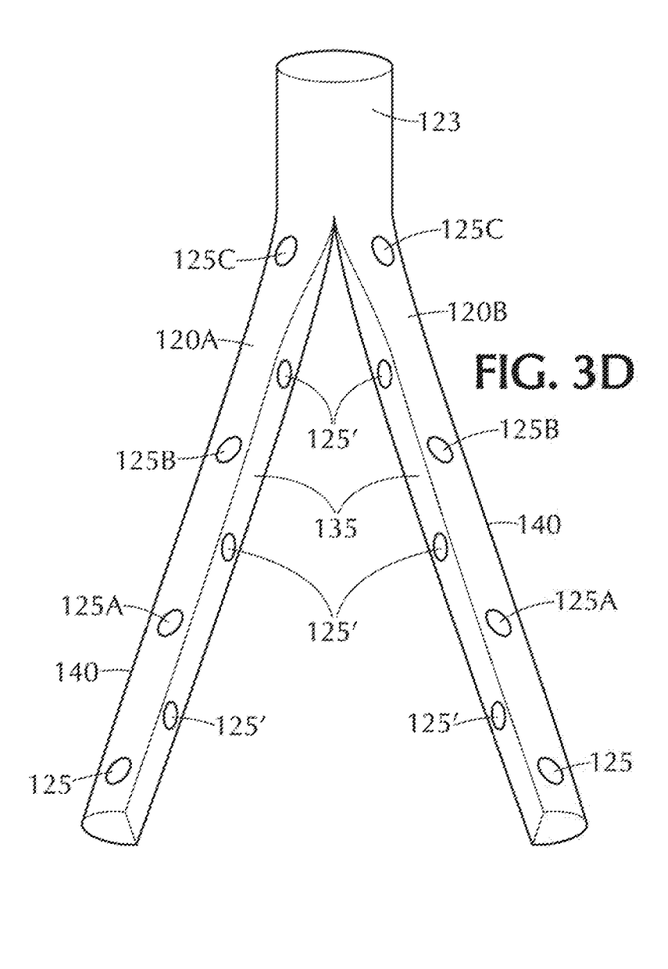

FIGS. 3A-3D depict the drainage catheter of FIG. 2A at four sequential stages in time following implantation. As seen in the different stages depicted in FIGS. 3A-3D, each branch lumen 120a, 120b has a plurality of holes, openings or pores defined radially outward therethrough its outer perimeter wall. The holes 125 are differentiated based on their location, i.e., whether the hole is defined in the first outer surface section 135 (as denoted by reference element numbers 125, 125A, 125B, 125C) or in the second outer surface section 140 (as denoted by reference element number 125') of the outer perimeter of a single distinct branch lumen. Except for an inlet opening at the interface with the plural branch lumen 120A, 120B and an opposite outlet opening, no other holes, openings or pores are defined in the outer radial perimeter of the central lumen 123. Adjacent, proximate, neighboring or closest hole centers (when viewed in an axial direction) defined in the first and second outer surface sections 135, 140, respectively, of a single distinct branch lumen are preferably offset or staggered from one another in a lateral direction by a lateral offset distance "X" (as illustrated in FIG. 3D) so that no two hole centers defined in the first and second outer surface sections of a single branch lumen are aligned at the same position in an axial direction relative to its distal end (i.e., non-coaxial). Such staggering or lateral offset distance "X" between hole centers of adjacent/opposing holes is preferably greater than or equal to the hole diameter, wherein the diameter of all holes are equal. Such offset of the holes 125' defined in the first outer surface section 135 relative to the holes (125, 125A, 125B, 12C) defined in the second outer surface section 140 for a single distinct branch lumen reduces or prohibits ingrowth of the choroid plexus through the holes between the first and second outer surface sections. If not for the inventive lateral offset distance, alignment at the same axial position relative to the distal end of the holes defined in the first and second outer surface sections of a single branch lumen, the catheter would be more susceptible to ingrowth of the choroid plexus therethrough the holes and potential clogging.

Figure 2B:
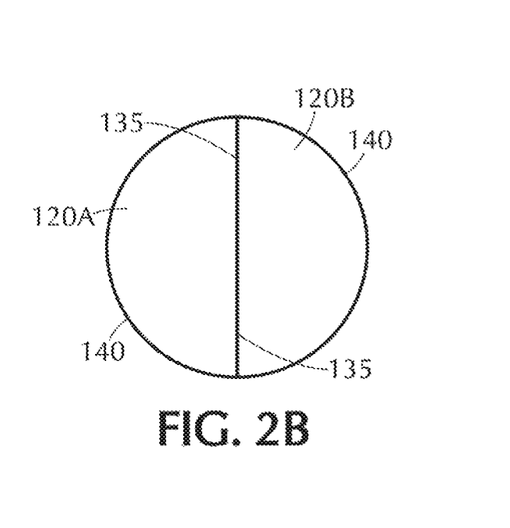
FIG. 2B is a cross-sectional view of the catheter of FIG. 2A along line I-I.

Prior to implantation (as depicted in FIGS. 2A & 2B), direct physical contact among the first outer surface sections 135 of the plural branch lumen 120A, 120B prevent or prohibit passage of any fluid through holes (125') defined in the first outer surface sections 135 of each of the distinct branch lumen 120A, 120B. Accordingly, the first outer surface sections 135 among the plural distinct branch lumen 120A, 120B are complementary in shape so that when in direct physical contact with one another the passage of any bodily fluid through the holes 125' defined therein is prevented or prohibited.

Blocking members 130 (e.g., radial straps, rings or bands) close off, mask or otherwise prohibit any fluid passing through the holes (125, 125A, 125B, 125C) defined in the second outer surface sections 140 of each of the plural distinct branch lumen 120A, 120B. At time zero ($t_0$) (i.e., at time of implantation), at least two outer patent holes 125 allow for drainage of bodily fluid immediately upon implantation. These two outer patent holes 125 positioned closest to the distal end 110 and defined in the second outer surface section 140 remain unmasked, patent or open at all times (including prior to and during implantation in the body). With the subsequent passage of time, for each blocking member 130 that dissolves, absorbs or degrades at least two holes per each distinct branch lumen will be unmasked/patent. In a preferred embodiment, each distinct branch lumen 120a, 120b has two outer patent holes 125 defined in the second outer surface section 140 closest to the distal end 110 that remain unmasked, patent or open at all times (i.e., these outer patent holes 125 are never deliberately closed off or masked by a blocking member or any other structural feature). Thus, outer patent holes 125 closest to the distal end 110 remain open at all times to allow, immediately upon implantation of the catheter in the body (while the remaining holes are masked or closed off either by a blocking member or physical contact among the first outer surface sections of the branch lumen), drainage therethrough the bodily fluid at a desired pressure or flow rate.

Starting from the distal end 110 and advancing axially toward the proximal end 105 of the catheter 100, the remaining holes 125A, 125B, 125C disposed at different positions in an axial direction and defined in the outer perimeter wall of the second outer surface section 140 of each distinct branch lumen 120A, 120B are temporarily completely deliberately masked, closed off or completely occluded by a corresponding blocking member (for example, radial strap, ring or band) 130A, 130B, 130C made of bioabsorbable, biodegradable or bioresorbable material that prohibits or prevents the passage of any bodily fluid through any of the holes covered by that particular blocking member. In a one-to-one correspondence, a single blocking member may be sized and configured to close off and prevent fluid from entering one or more holes defined in the second outer surface section 140 associated with a single branch lumen 120A, 120B. Preferably, a single blocking member may be sized and configured to mask or close off one or more holes associated with each of the plural distinct branch lumen 120A, 120B thereby preventing bodily fluid from entering therethrough. With the exception of the one or more holes 125 disposed closest to the distal end 110 of the catheter which remain unmasked, open or unobstructed at all times (i.e., not deliberately masked or closed off by a blocking member or other structural feature), all remaining holes 125A, 125B, 125C defined in the second outer surface section 140 of each of the plural branch lumen 120A, 120B are initially and temporarily (for a predetermined period of time following implantation and prior to being completely absorbed, degraded or dissolved in the body) closed off or masked by an associated or corresponding blocking member 130A, 130B, 130C made of bioabsorbable, biodegradable or bioresorbable material prohibiting any bodily fluid from entering therein.

Referring to the exemplary embodiment illustrated in FIG. 2A, three blocking members 130A, 130b, 130c of bioabsorbable, biodegradable or bioresorbable material are depicted to mask, cover, block or obstruct holes 125A, 125B, 125C defined in the second outer surface section 140 of each of the plural distinct branch lumen 120A, 120B. Of course, the present invention may be modified, as desired, whereby the catheter has any number of one or more blocking members 130 so long as, with the exception of at least two holes 125 disposed closest to the distal end 110 of the catheter, all remaining holes 125A, 125B, 125C defined in the second outer surface section 140 of each of the plural branch lumen 120A, 120B are deliberately, initially and temporarily masked, covered or closed off by a corresponding blocking member.

In accordance with the present invention, each blocking member 130A, 130B, 130C is made of a bioabsorbable, biodegradable or bioresorbable material that is designed to completely absorb, degrade or dissolve in the body at different sequentially staggered time intervals or periods. By way of illustrative example only, a first blocking member 130A masks a hole 125A defined in the second outer surface section 140 of each of the plural distinct branch lumen 120A, 120B. The first blocking member 130A is made of a bioabsorbable, biodegradable or bioresorbable material that is designed to completely absorb, degrade or dissolve in the body upon the passage of a second time period or interval ($t_2$) following implantation in the body (representative of a second stage). A second blocking member 130B masks a hole 125B defined in the second outer surface section 140 of each of the plural branch lumen 120A, 120B. The second blocking member 130B is made of a bioabsorbable, biodegradable or bioresorbable material that is designed to completely absorb, degrade or dissolve in the body upon the passage of a third time period or interval ($t_3$) following implantation in the body (representative of a third stage). A third blocking member 130C masks a hole 125C defined in the second outer surface section 140 of each of the plural branch lumen 120A, 120B. The third blocking member 130C is also made of a bioabsorbable, biodegradable or bioresorbable material that is designed to completely absorb, degrade or dissolve in the body upon the passage of a fourth time period or interval ($t_4$) following implantation in the body (representative of a fourth stage). In this illustrative example the second time period or interval ($t_2$)=1 week; the third time period or interval ($t_3$)=6 weeks; while the fourth time period or interval ($t_4$)=6 months. Hence, the bioabsorbable material blocking members (130A, 130B, 130C) are designed to completely absorb, degrade or dissolve in the body in a time sequential staggered manner wherein the time intervals are selected so that $t_1<t_2<t_3<t_4$. Preferably, all blocking members are dissolved and hence all drainage holes are exposed, within approximately one year of implantation. Thus, the blocking member 130A closest to the distal end 110 has the shortest life span prior to completely dissolving or absorbing in the body. Each successive blocking member 130B advancing axially toward the proximal end 105 of the catheter has a longer life span (i.e., passage of time prior to completely dissolving or absorbing in the body) than its predecessor. While the blocking member 130C that is closest to the proximal end 105 (farthest from the distal end 110) of the catheter has the longest life span prior to completely dissolving, degrading or absorbing in the body. The formulation and/or dimensions (e.g., thickness) of the bioabsorbable material for manufacturing each blocking member may be selected to achieve the desired time period for complete absorption, degradation or dissolution in the body. Thus, the blocking members may be made of different materials or the same material and/or differ or be the same in dimension. It is also noted that despite the exemplary embodiment depicting any one blocking member masking only a single hole defined in each branch lumen, it is contemplated and within the intended scope of the present invention for any one blocking member to mask more than one hole defined in any particular branch lumen, or that any one blocking member need not necessarily mask off a hole defined in every one of the plural lumen (e.g., a single blocking member may be configured to mask a hole defined in only one branch lumen). The holes in the second outer surface section 140 masked off by a particular blocking member 130 need not be the same in number for each distinct branch lumen. It is also contemplated that a particular blocking member need not mask off or cover any hole defined in the second outer surface section 140 of certain distinct branch lumen.

Those holes in the drainage catheter closest to the valve (i.e., closest to the proximal end 105 of the drainage catheter) drain approximately 80% of the bodily fluid. Thus, in the unfortunate event that these holes in the drainage catheter closest to the valve become obstructed, clogged or occluded the drainage catheter may undesirably cease to operate as intended to maintain a desired pressure or flow rate. Staggering the time period for 20 degrading, dissolving or absorbing of the blocking members exposes over time new open holes closer to the valve (i.e., closer to the proximal end 105 of the catheter) thereby extending the lifespan and operation of the drainage catheter even in the presence of obstruction or blockage of open holes.

Referring to FIG. 2A, prior to implantation in the body, the dip coating or covering 115 of bioabsorbable, biodegradable or bioresorbable material covering the distal tip of the catheter secures the plural separate distinct branch lumen 120A, 120B together thereby aiding insertion of the catheter through the ventricle or other passageway to a desired target location or site within the body. Immediately upon implantation at a target location or site within the body (at time t=0), the drainage catheter 100 in accordance with the present invention allows for free passage of body fluid at the desired pressure or flow rate through the two or more patent holes 125 disposed closest to the distal end 110 of the catheter that are never intentionally masked, covered or closed off by a blocking member (i.e., prior to implantation as well as over the entire operating lifespan of the catheter, these holes 125 are never masked off). Once implanted, over time the dip coating or covering 115 of the catheter begins to absorb, degrade or dissolve in the body. Once the dip coating or covering 115 has completely absorbed, degraded or dissolved (as shown in FIG. 3A, after passage of a time ($t_1$)), in the absence of such external applied force applied by the dip coating, the distal end of the distinct branch lumen 120A, 120B (as a result of the shape memory material from which it is manufactured) automatically returns to its non-deformed state and begins separating from one another starting at the distal end 110. Separation of the distinct branch lumen 120A, 120B in an axial direction is stopped by the presence of the first blocking member 130A secured about the outer perimeter (i.e., disposed about the second outer surface sections 140 of the plural distinct branch lumen 120A, 120B). In the exemplary embodiment depicted in FIG. 3A, such initial separation, starting from its distal end, of the branch lumen 120A, 120B from one another exposes a hole 125' defined in the first outer surface section 135 of each of the distinct branch lumen (previously masked or covered by the complementary mating first outer surface sections 135 of the branch lumen 120A, 120B in direct physical contact with one another).

FIG. 3B depicts the catheter after the passage of a second time period ($t_2$) following implantation of the catheter in the body, wherein the first blocking member 130A closest to the distal end 110 of the catheter 100 is completely dissolved, degraded or absorbed in the body. The complete dissolution, degradation or absorption of the first blocking member 130A automatically triggers the following simultaneous events: (i) the hole 125A defined in the second outer surface section 140 of each of the plural branch lumen 120A, 120B is now completely exposed allowing the free flow of bodily fluid therethrough; and (ii) due to the shape memory material from which it is manufactured, in response to the withdrawal of the external force previously applied by the first blocking member 130A, the plural distinct branch lumen 120A, 120B begin to further separate and flare radially outward exposing another hole 125' defined in the first outer surface section 135 of each of the plural branch lumen 120A, 120B allowing the free passage of bodily fluid therethrough.

With the passage of time, at the expiration of a third time period ($t_3$) following implantation of the catheter in the body, the second blocking member 130B completely dissolves, degrades or absorbs in the body, as shown in FIG. 3C. As additional blocking members dissolve, degrade or absorb new holes defined in both the first outer surface section 135 and the second outer surface section 140 of each of the plural branch lumen 120A, 120B become exposed allowing the free passage of bodily fluid therethrough. FIG. 3D shows the catheter after the passage of a fourth time period ($t_4$) following implantation of the catheter in the body with the third blocking member 130C farthest from the distal end 110 of the catheter 100 completely dissolved, degraded or absorbed in the body. All holes in the first and second outer sections of all of the branch lumen are now exposed allowing the free passage of bodily fluid therethrough.

Figure 4:
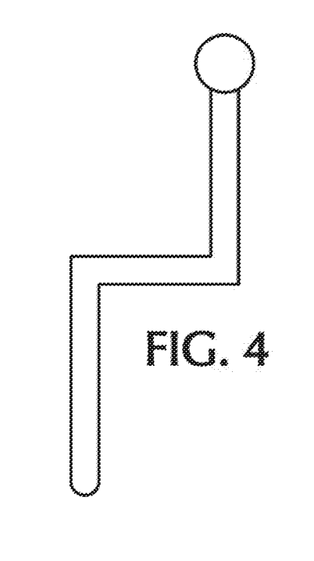
FIG. 4 shows a side view of a lateral offset stylet to aid in insertion of the catheter of FIG. 2A.

Configuration of the two branch lumen 120A, 120B feeding into a common central lumen 123 introduces a lateral offset of the center of the passageway of the central lumen 123 relative to that of the center of the passageway of either respective distinct branch lumen 120A, 120B. To aid in insertion of the catheter into a ventricle or other passageway of the body an offset stylet 200 (as depicted in FIG. 4) is employed. The lateral offset (d) of the stylet 200 corresponds to the distance separation of the center of the passageway of the common central lumen 123 relative to that of the center of the passageway of either distinct branch lumen 120A, 120B.

Figure 5A:
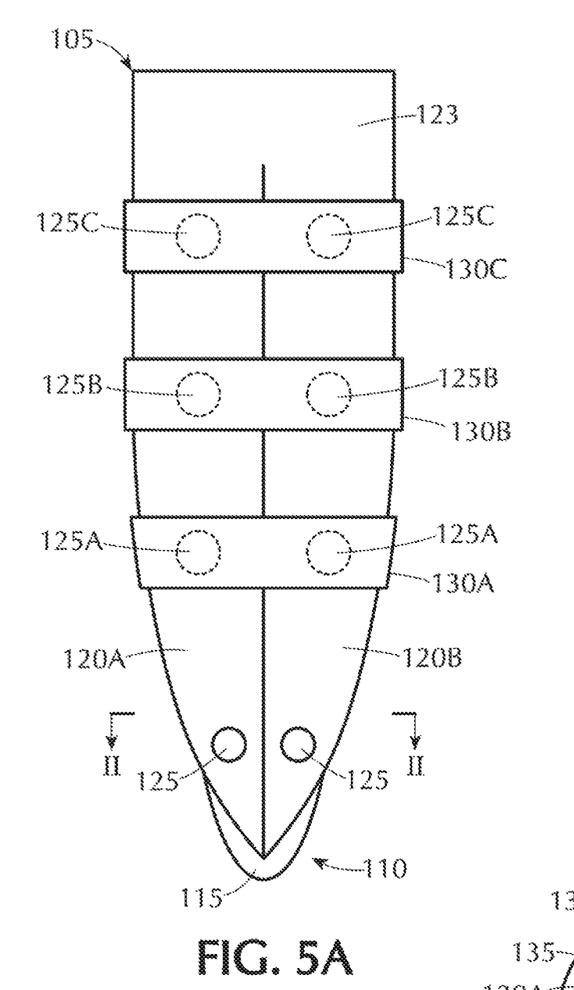
FIG. 5A is a partial side view of a distal end of another exemplary drainage catheter in accordance with the present invention, prior to implantation in the human body, having three branch lumen.
Figure 5B:
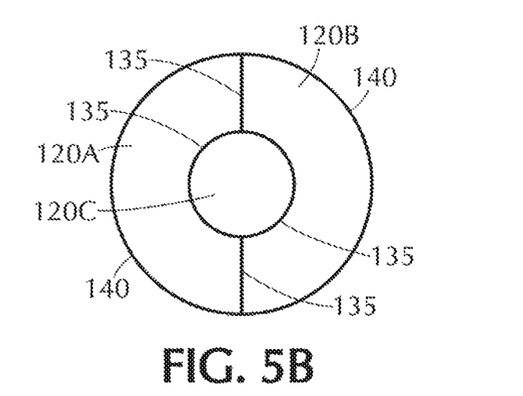
FIG. 5B is a cross-sectional view of the catheter of FIG. 5A along line II-II.
Figure 6A:
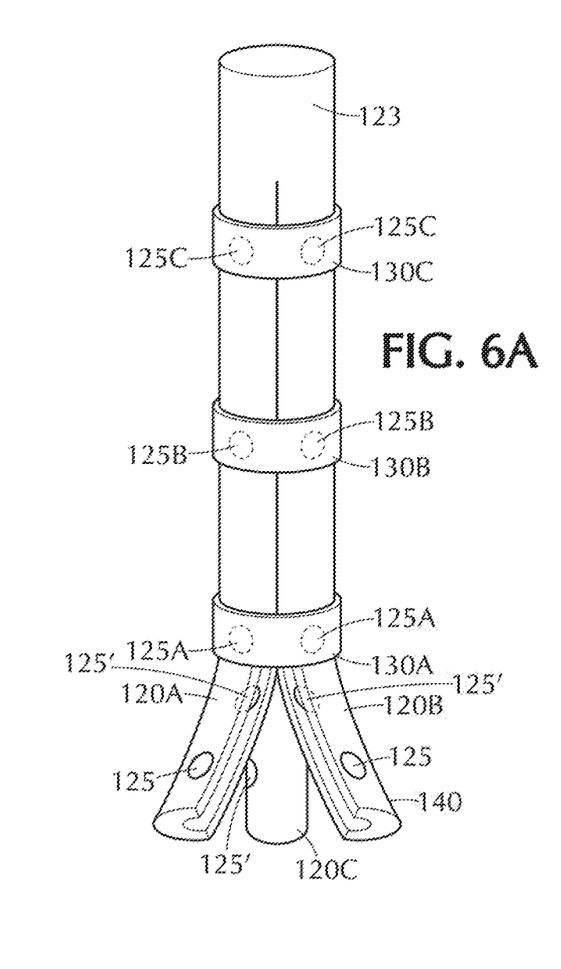
FIGS. 6A-6D are partial side views of the drainage catheter of FIG. 5A at four different stages in time.
Figure 6B:
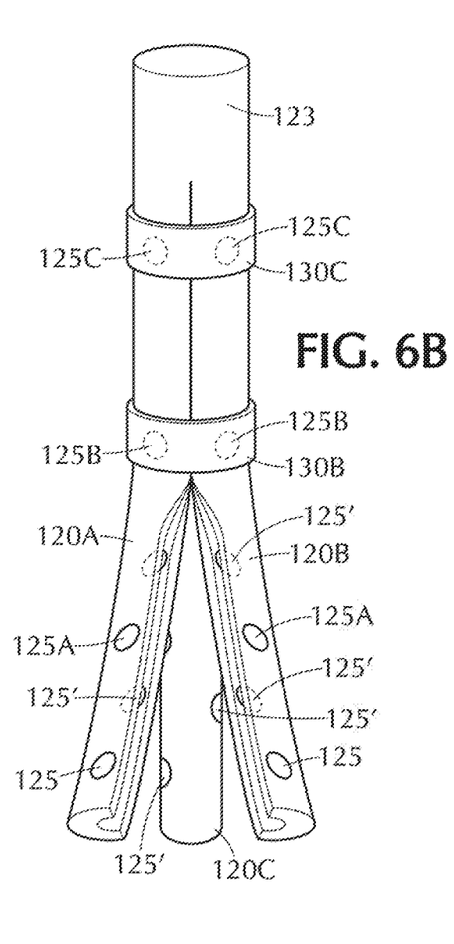
Figure 6C:
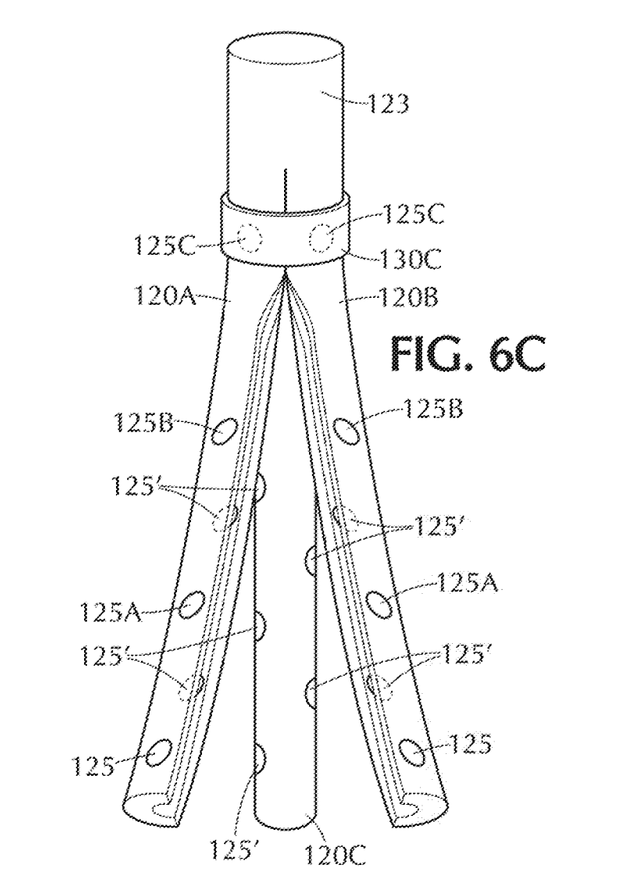
Figure 6D:
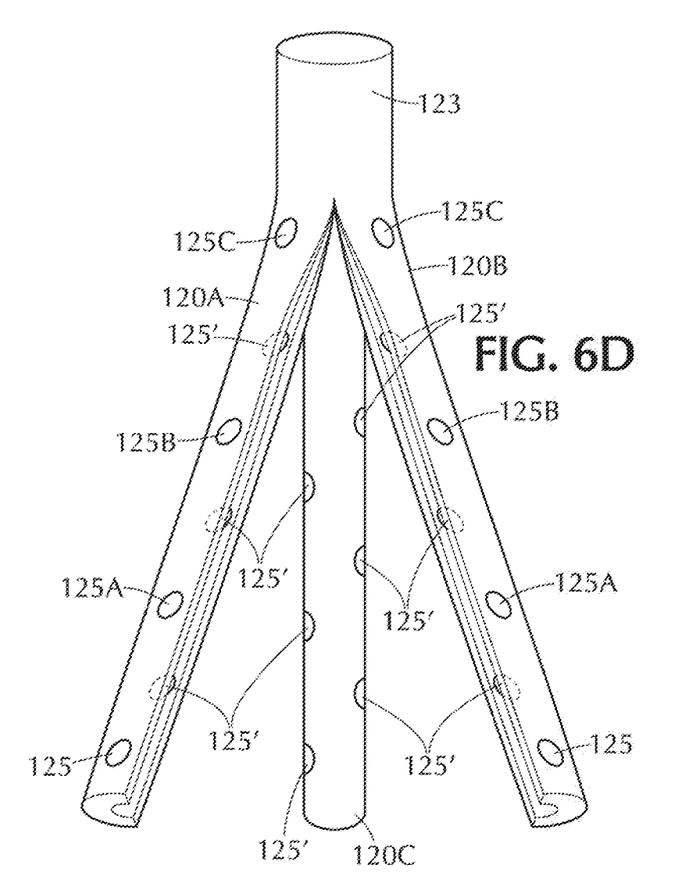

In an alternative embodiment, the distal end of the catheter 100 may be split or separable into three distinct branch lumen 120A, 120B, 120C, rather than two. FIG. 5A is a partial side view of an exemplary catheter in accordance with the present invention having three branch lumen. The features shown are the same as those discussed above with respect to FIG. 2A and thus will not be described further. A cross-sectional view of the catheter of FIG. 5A along the lines II-II is depicted in FIG. 5B. From this cross-sectional view, the different configuration is evident from that of FIG. 2B. A third branch lumen 120C, coaxial with the common central lumen 123, is completely surrounded or radially enclosed by the other two distinct branch lumen 120A, 120B, while in an assembled or secured state (prior to implantation). In this alternative embodiment, the outer perimeter of each of the first and second branch lumen 120A, 120B includes a first outer surface section 135 and a second outer surface section 140. The third branch lumen 120C has an outer perimeter comprising only a first outer surface section 135. The third branch lumen 120C does not have an associated second outer surface section 140 since, while in an assembled or secured state, every portion of its outer perimeter is in direct physical contact with the first outer surface sections 135 of the other two branch lumen 120A, 120B. Due to the fact that the third branch lumen 120C is coaxial with the common central lumen 123, this specific configuration eliminates the need for an offset stylet (as shown in FIG. 4). Instead a conventional linear stylet may be utilized to aid in insertion of the catheter shown in FIGS. 5A & 5B during implantation.

As depicted in the time sequential staggered illustrations of FIGS. 6A-6D, the dissolving, degrading or absorption of the tip coating 115, followed thereafter by the first blocking member 130A, the second blocking member 130B and lastly the third blocking member 130C over time exposes new holes defined in: (i) the first outer surface sections 135 of the first, second and third branch lumen 120A, 120B, 120C; and (ii) the second outer surface sections 140 of only the first and second branch lumen (120A, 120B). With this particular three branch lumen configuration, in the assembled and secured state prior to implantation, all holes (excluding the inlet opening and outlet opening of the axial passageway through the lumen) defined in the outer radial perimeter of the third branch lumen 120C are masked, covered or closed off by the first outer surface section 135 of the other two branch lumen 120A, 120B. No portion of the outer perimeter of the third branch lumen 120C is deliberately masked off or covered at any time by a blocking member of bioabsorbable material. Other configurations for three branch lumen are contemplated and within the intended scope of the present invention. For example, similar to the two hemispherical cross-sectional shaped branch lumen depicted in FIG. 2B, the cross-sectional shape of the three branch lumen may represent three equal one third wedges together forming a complete circle. In such design, the outer perimeter of each of the three branch lumen has a first outer surface section 135 in direct physical contact with one another and a second outer surface section 140 that is not in physical contact with any other first or second outer surface section. Of course, the cross-sectional shape of the plural branch lumen may be modified.

Thus, the present inventive drainage catheter has an extended lifespan in comparison to that of conventional devices by exposing, unmasking or uncovering new holes in a time sequential staggered manner. If one or more holes in the drainage catheter become obstructed, blocked or occluded, at a subsequent point in time new holes (previously masked, covered or closed off) will be exposed for the first time to allow the free passage of bodily fluid therethrough thereby extending the operational lifespan of the drainage catheter. Furthermore, in the event that a single branch or leg of the catheter should become obstructed, blocked or occluded, the bodily fluid may continue to be drained through the remaining one or more branches or legs of the catheter.

Thus, while there have been shown, described, and pointed out fundamental novel features of the invention as applied to a preferred embodiment thereof, it will be understood that various omissions, substitutions, and changes in the form and details of the devices illustrated, and in their operation, may be made by those skilled in the art without departing from the spirit and scope of the invention. For example, it is expressly intended that all combinations of those elements and/or steps that perform substantially the same function, in substantially the same way, to achieve the same results be within the scope of the invention. Substitutions of elements from one described embodiment to another are also fully intended and contemplated. It is also to be understood that the drawings are not necessarily drawn to scale, but that they are merely conceptual in nature. It is the intention, therefore, to be limited only as indicated by the scope of the claims appended hereto.

Every issued patent, pending patent application, publication, journal article, book or any other reference cited herein is each incorporated by reference in their entirety.

What is claimed is:

1. An implantable valve assembly having an extended operational lifespan, comprising:
   a drainage catheter having a proximal end and an opposite distal end terminating in a distal tip; the drainage catheter comprising a single central lumen disposed proximate the proximal end and having a single central passageway defined longitudinally therethrough; between the proximal and distal ends of the drainage catheter, the single central lumen transitions at an interface into a plurality of distinct branch lumen made of a shape memory material; each of the plurality of distinct branch lumen having associated therewith a single branch passageway defined longitudinally therethrough; the single branch passageway of each of the plurality of distinct branch lumen being in fluid communication with the single central passageway of the single central lumen;

a dip coating of bioabsorbable material covering an outer surface of the distal end of the drainage catheter; the dip coating securing the plural distinct branch lumen in direct physical contact with one another from the distal end of the drainage catheter to the interface with the single central lumen; and wherein each of the plurality of distinct branch lumen has an outer perimeter comprising at least one of a first outer surface section and a second outer surface section; together the first and second outer surface sections of a particular distinct branch lumen of the plurality of distinct branch lumen comprise an entire outer radial perimeter; while in a secured state with the plurality of distinct branch lumen held together by the dip coating: (i) the first outer surface section of each of the plurality of distinct branch lumen is in direct physical contact with the first outer surface section of at least one other branch lumen in a longitudinal direction from the interface to the distal end of the catheter; and (ii) the second outer surface section of each of the plurality of distinct branch lumen is not in physical contact with either the first or second outer surface sections of any other branch lumen;

wherein the dip coating covers the second outer surface section of each of the plurality of distinct branch lumen, without covering the first outer surface section of each of the plurality of distinct branch lumen;

wherein each of the plurality of distinct branch lumen has a plurality of holes defined radially outward therethrough in the first and the second outer surface sections; while in the secured state with the plurality of distinct branch lumen held together by the dip coating a fluid is prohibited from passing through the plurality of holes defined in the first outer surface sections of any of the plurality of distinct branch lumen.

2. The assembly in accordance with claim 1, wherein in an axial direction adjacent hole centers of each of the holes defined in the first and second outer surface sections, respectively, of the particular distinct branch lumen of the plurality of distinct branch lumen are staggered from one another by a predetermined lateral offset distance so that the adjacent hole centers defined in the first and second outer surface sections of the particular distinct branch lumen are non-linearly arranged in an axial direction.

3. The assembly in accordance with claim 2, wherein the predetermined lateral offset distance is greater than or equal to a diameter of the hole, wherein the diameter of each hole is substantially equal.

4. The assembly in accordance with claim 1, wherein the bioabsorbable material of the dip coating is absorbed upon expiration of a first predetermined time period in a range of 72 hrs. to 168 hrs.

5. The assembly in accordance with claim 1, wherein in an absence of an applied external force, the plural distinct branch lumen extend radially outward from the single central lumen; upon the application of the external force, the plurality of distinct branch lumen are deformable radially inward so as to physically contact one another in an axial direction from the interface with the single central lumen to the distal end of the drainage catheter forming an assembled cylinder having a diameter substantially equal to and coaxial with that of the single central lumen.

6. The assembly in accordance with claim 1, further comprising at least one blocking member made of a bioabsorbable material masking the holes disposed at approximately the same axial distance from the distal end of the drainage catheter in the second outer surface sections of each of the plurality of distinct branch lumen prohibiting any fluid entering therein.

7. The assembly in accordance with claim 6, wherein the plurality of holes includes: (i) at least two outer patent holes positioned closest to the distal end of the drainage catheter and defined in the second outer surface section of the plural distinct branch lumen that are unmasked allowing entry of fluid therein; and (ii) all remaining holes defined in the first and second outer surface sections of the plurality of distinct branch lumen; with the exception of the at least two outer patent holes positioned closest to the distal end of the drainage catheter and defined in the second outer surface section of the plurality of distinct branch lumen that are unmasked allowing entry of fluid therein, the passage of the fluid through the all remaining holes defined in the first and second outer surface sections of the plurality of distinct branch lumen is prohibited by a corresponding blocking member or physical contact among the first outer surface sections of the plurality of distinct branch lumen.

8. The assembly in accordance with claim 7, wherein the corresponding blocking member is made of a bioabsorbable, biodegradable or bioreabsorbable material that is completely absorbable, degradable or reabsorbable; and at least two holes per each of the plurality of distinct branch lumen are masked by the corresponding blocking member.

9. An implantable valve assembly having an extended operational lifespan, comprising:

a drainage catheter having a proximal end and an opposite distal end terminating in a distal tip; the drainage catheter comprising a single central lumen disposed proximate the proximal end and having a single central passageway defined longitudinally therethrough; between the proximal and distal ends of the drainage catheter, the single central lumen transitions at an interface into a plurality of distinct branch lumen made of a shape memory material, each of the plurality of distinct branch lumen having associated therewith a single branch passageway defined longitudinally therethrough; the single branch passageway of each of the plurality of distinct branch lumen being in fluid communication with the single central passageway of the single central lumen;

a dip coating of bioabsorbable material covering an outer surface of the distal end of the drainage catheter, the dip coating securing the plural distinct branch lumen in direct physical contact with one another from the distal end of the drainage catheter to the interface with the single central lumen;

wherein each of the plurality of distinct branch lumen has an outer perimeter comprising at least one of a first outer surface section and a second outer surface section; together the first and second outer surface sections of a particular distinct branch lumen of the plurality of distinct branch lumen comprise an entire outer radial perimeter; while in a secured state with the plurality of distinct branch lumen held together by the dip coating: (i) the first outer surface section of each of the plurality of distinct branch lumen is in direct physical contact with the first outer surface section of at least one other branch lumen in a longitudinal direction from the interface to the distal end of the catheter, and (ii) the second outer surface section of each of the plurality of distinct branch lumen is not in physical contact with either the first or second outer surface sections of any other branch lumen;

wherein each of the plurality of distinct branch lumen has a plurality of holes defined radially outward therethrough in the first and the second outer surface sections, while in the secured state with the plurality of distinct branch lumen held together by the dip coating a fluid is prohibited from passing through the plurality of holes defined in the first outer surface sections of any of the plurality of distinct branch lumen; and at least one blocking member made of a bioabsorbable material masking the holes disposed at approximately the same axial distance from the distal end of the drainage catheter in the second outer surface sections of each of the plurality of distinct branch lumen prohibiting any fluid entering therein;

wherein the assembly comprises a plurality of non-overlapping blocking members sequentially arranged one-after-the other and separated from one another in an axial direction about a perimeter of the drainage catheter; each of the plurality of blocking members is a ring disposed about the outer perimeter of the drainage catheter; and each of the plurality of blocking members is made of a bioabsorbable material selected with a formulation and/or dimension to completely absorb at different sequentially staggered time periods such that: a first blocking member of the plurality of blocking members is disposed closest to the distal end of the drainage catheter has a shortest life span prior to completely absorbing; advancing in an axial direction away from the distal end of the drainage catheter, each successive blocking member of the plurality of blocking members has a longer life span prior to completely absorbing than a preceding blocking member of the plurality of blocking members positioned closer to the distal end of the drainage catheter; and, a last blocking member of the plurality of blocking members positioned farthest from the distal end of the drainage catheter has a longest life span prior to completely absorbing than any preceding blocking member of the plurality of blocking members positioned closer to the distal end of the drainage catheter.

10. The assembly in accordance with claim 1, further comprising a lateral offset stylet; wherein a lateral offset of the lateral offset stylet corresponds to a distance separation of a center of the single central passageway of the single central lumen relative to that of a center of the single branch passageway of an associated one of the plurality of distinct branch lumen.

11. A method for using an implantable valve assembly having an extended operational lifespan, wherein the implantable valve assembly includes a drainage catheter having a proximal end and an opposite distal end; the drainage catheter having a single central lumen disposed proximate the proximal end and having a single central passageway defined longitudinally therethrough; between the proximal and distal ends of the drainage catheter, the single central lumen transitions at an interface into a plurality of distinct branch lumen made of a shape memory material; each of the plurality of distinct branch lumen having associated therewith a single branch passageway defined longitudinally therethrough; the single branch passageway of each of the plurality of distinct branch lumen being in fluid communication with the single central passageway of the single central lumen; a dip coating of bioabsorbable material is covering an outer surface of the distal end of the drainage catheter; wherein each of the plurality of distinct branch lumen has an outer perimeter comprising at least one of a first outer surface section and a second outer surface section; together the first and second outer surface sections of a particular distinct branch lumen of the plurality of distinct branch lumen comprise an entire outer radial perimeter; and wherein each of the plurality of distinct branch lumen has a plurality of holes defined radially outward therethrough in the first and the second outer surface sections, the method comprising the steps of:

during implantation, advancing the drainage catheter to a target site while the plurality of distinct branch lumen are secured in direct physical contact with one another from the distal end of the drainage catheter to the interface of the single central lumen via the dip coating; while in a secured state with the plurality of distinct branch lumen held together by the dip coating: (i) the first outer surface section of each of the plurality of distinct branch lumen is in direct physical contact with the first outer surface section of at least one other branch lumen in a longitudinal direction from the interface with the single central lumen to the distal end of the catheter prohibiting fluid from entering holes defined in the first outer surface sections of any of the plurality of distinct branch lumen; and (ii) the second outer surface section of each of the plurality of distinct branch lumen is not in physical contact with either the first or second outer surface sections of any other branch lumen;

wherein the dip coating covers the second outer surface section of each of the plurality of distinct branch lumen, without covering the first outer surface section of each of the plurality of distinct branch lumen.

12. The method in accordance with claim 11, wherein in the secured state secured together by the dip coating the plurality of distinct branch lumen are deformed radially inward so as to physically contact one another in a longitudinal direction from the interface with the single central lumen to the distal end of the drainage catheter forming an assembled cylinder having a diameter substantially equal to and coaxial with that of the single central lumen.

13. The method in accordance with claim 11, wherein in an axial direction adjacent hole centers of the holes defined in the first and second outer surface sections, respectively, of the particular distinct branch lumen of the plurality of distinct branch lumen are staggered from one another by a predetermined lateral offset distance so that the adjacent hole centers defined in the first and second outer surface sections of the particular distinct branch lumen are non-linearly arranged in an axial direction.

14. The method in accordance with claim 11, further comprising the step of, upon expiration of a first predetermined passage of time in which the dip coating is completely absorbed, automatically the shape memory material of the plurality of distinct branch lumen returning to an original shape extending radially outward from the single central lumen so that starting from the distal end of the catheter a portion of the first outer surface sections of the plurality of distinct branch lumen separate from one another allowing fluid to enter the holes exposed in the first outer surface section that have separated from one another.

15. The method in accordance with claim 12, wherein the valve assembly includes a plurality of blocking members of which at least one of the plurality of blocking members is made of a bioabsorbable material masking the holes disposed at the same axial distance from the distal end of the drainage catheter in the second outer surface sections of each of the plurality of distinct branch lumen prohibiting any fluid entering therein.

16. The method in accordance with claim 15, wherein during implantation of the valve; wherein the plurality of holes includes: (i) at least two outer patent holes positioned closest to the distal end of the drainage catheter and defined in the second outer surface section of the plurality of distinct branch lumen that are unmasked allowing entry of fluid therein; and (ii) all remaining holes defined in the first and second outer surface sections of the plurality of distinct branch lumen; with the exception of the at least two outer patent holes positioned closest to the distal end of the drainage catheter and defined in the second outer surface section of the plurality of distinct branch lumen that are unmasked allowing entry of fluid therein, the passage of the fluid through the all remaining holes defined in the first and second outer surface sections of the plurality of distinct branch lumen is prohibited by a corresponding blocking member or physical contact among the first outer surface sections of the plurality of distinct branch lumen.

17. The method in accordance with claim 15, upon complete absorbing of each of the plurality of blocking members, at least two holes per each of the plurality of distinct branch lumen are unmasked allowing passage of the fluid therein.

18. The method in accordance with claim 15, wherein the valve assembly comprises a plurality of blocking members sequentially arranged one-after-the other in an axial direction about a perimeter of the drainage catheter; each of the plurality of blocking members is made of a bioabsorbable material selected with a formulation and/or dimension to completely absorb at different sequentially staggered time periods such that: a first blocking member of the plurality of blocking members disposed closest to the distal end of the drainage catheter has a shortest life span prior to completely absorbing; advancing in an axial direction away from the distal end of the drainage catheter, each successive blocking member of the plurality of blocking members has a longer life span prior to completely absorbing than a preceding block member of the plurality of blocking members positioned closer to the distal end of the drainage catheter; and, a last blocking member of the plurality of blocking members that is farthest from the distal end of the drainage catheter has a longest life span prior to completely absorbing than any preceding blocking member of the plurality of blocking members positioned closer to the distal end of the drainage catheter.

19. The method in accordance with claim 11, wherein the step of advancing the drainage catheter to the target site is performed using a lateral offset stylet; wherein a lateral offset of the lateral offset stylet corresponds to a distance separation of a center of the single central passageway of the single central lumen relative to that of a center of the single branch passageway of an associated one of the plurality of distinct branch lumen.

20. An implantable valve assembly having an extended operational lifespan, comprising:
a drainage catheter having a proximal end and an opposite distal end terminating in a distal tip; the drainage catheter comprising a single central lumen disposed proximate the proximal end and having a single central passageway defined longitudinally therethrough; between the proximal and distal ends of the drainage catheter, the single central lumen transitions at an interface into three distinct branch lumen including a first branch lumen, a second branch lumen and a third branch lumen, each of the three distinct branch lumen made of a shape memory material; each of the three distinct branch lumen having associated therewith a single branch passageway defined longitudinally therethrough; the single branch passageway of each of the three distinct branch lumen being in fluid communication with the single central passageway of the single central lumen; the single branch passageway of the third branch lumen is coaxial with the single central passageway of the single central lumen; and the third branch lumen is radially enclosed by the first and second branch lumen;
a dip coating of bioabsorbable material covering an outer surface of the distal end of the drainage catheter; the dip coating securing of the three distinct branch lumen in direct physical contact with one another from the distal end of the drainage catheter to the interface with the single central lumen; and
wherein each of the first and second branch lumen has an outer perimeter comprising a first outer surface section and a second outer surface section; the third branch lumen has an outer perimeter comprising only a first outer surface section;
while in a secured state with the three distinct branch lumen held together by the dip coating: (i) the first outer surface section of each of the first and second branch lumen is in direct physical contact with the first outer surface section of the third branch lumen in a longitudinal direction from the interface to the distal end of the catheter; and (ii) the second outer surface section of each of the first and second branch lumen is not in physical contact;
wherein each of the three distinct branch lumen has a plurality of holes defined radially outward therethrough in the first outer surface sections; while in the secured state with the three distinct branch lumen held together by the dip coating a fluid is prohibited from passing through the plurality of holes defined in the first outer surface sections of any of the three distinct branch lumen.

21. The implantable valve assembly in accordance with claim 20, wherein in an axial direction adjacent hole centers of each of the holes defined in the first and second outer surface sections, respectively, of the first and second branch lumens are staggered from one another by a predetermined lateral offset distance so that the adjacent hole centers defined in the first and second outer surface sections of the first and second branch lumen are non-linearly arranged in an axial direction.

22. The implantable valve assembly in accordance with claim 21, wherein the predetermined lateral offset distance is greater than or equal to a diameter of the hole, wherein the diameter of each hole is substantially equal.

23. The implantable valve assembly in accordance with claim 20, wherein the bioabsorbable material of the dip coating is absorbed upon expiration of a first predetermined time period in a range of 72 hrs. to 168 hrs.

24. The implantable valve assembly in accordance with claim 20, wherein in an absence of an applied external force, the first and second branch lumen extend radially outward from the single central lumen; upon the application of the external force, the plurality of distinct branch lumen are deformable radially inward so as to physically contact one another and the first outer surface section of the third branch lumen in an axial direction from the interface with the single central lumen to the distal end of the drainage catheter forming an assembled cylinder having a diameter substantially equal to and coaxial with that of the single central lumen.

25. The implantable valve assembly in accordance with claim 20, further comprising at least one blocking member made of a bioabsorbable material masking the holes disposed at approximately the same axial distance from the distal end of the drainage catheter in the second outer surface section of each of the first and second branch lumen prohibiting any fluid entering therein.

26. The implantable valve assembly in accordance with claim 25, wherein the plurality of holes includes: (i) at least two outer patent holes positioned closest to the distal end of the drainage catheter and defined in the second outer surface section of the first and second branch lumen that are unmasked allowing entry of fluid therein; and (ii) all remaining holes defined in the first and second outer surface sections of the first and second branch lumen; with the exception of the at least two outer patent holes positioned closest to the distal end of the drainage catheter and defined in the second outer surface section of the first and second branch lumen that are unmasked allowing entry of fluid therein, the passage of the fluid through the all remaining holes defined in the first and second outer surface sections of the first and second branch lumen is prohibited by a corresponding blocking member or physical contact with the first outer surface section of the third branch lumen.

27. The implantable valve assembly in accordance with claim 26, wherein the corresponding blocking member is made of a bioabsorbable, biodegradable or bioreabsorbable material that is completely absorbable, degradable or reabsorbable; and at least two holes per each of the first and second branch lumen are masked by the corresponding blocking member.

28. The implantable valve assembly in accordance with claim 25, wherein the assembly comprises a plurality of non-overlapping blocking members sequentially arranged one-after-the other and separated from one another in an axial direction about a perimeter of the drainage catheter; each of the plurality of blocking members is a ring disposed about the outer perimeter of the drainage catheter; and each of the plurality of blocking members is made of a bioabsorbable material selected with a formulation and/or dimension to completely absorb at different sequentially staggered time periods such that: a first blocking member of the plurality of blocking members is disposed closest to the distal end of the drainage catheter has a shortest life span prior to completely absorbing; advancing in an axial direction away from the distal end of the drainage catheter, each successive blocking member of the plurality of blocking members has a longer life span prior to completely absorbing than a preceding blocking member of the plurality of blocking members positioned closer to the distal end of the drainage catheter; and, a last blocking member of the plurality of blocking members positioned farthest from the distal end of the drainage catheter has a longest life span prior to completely absorbing than any preceding blocking member of the plurality of blocking members positioned closer to the distal end of the drainage catheter.

29. The implantable valve assembly in accordance with claim 20, further comprising a lateral offset stylet; wherein a lateral offset of the lateral offset stylet corresponds to a distance separation of a center of the single central passageway of the single central lumen relative to that of a center of the single branch passageway of the first or second branch lumen.

* * * * *